US012723183B2

(12) United States Patent
Bugana et al.

(10) Patent No.: US 12,723,183 B2
(45) Date of Patent: Sep. 1, 2026

(54) HOT-MELT ADHESIVES COMPRISING BUTENE-1 POLYMERS AND SHOWING PECULIAR THERMAL CHARACTERISTICS

(71) Applicant: SAVARE' I.C. S.R.L., Milan (IT)

(72) Inventors: Alberto Bugana, Milan (IT); Italo Corzani, Milan (IT)

(73) Assignee: SAVARE' I.C. S.R.L., Milan (IT)

( * ) Notice: Subject to any disclaimer, the term of this patent is extended or adjusted under 35 U.S.C. 154(b) by 178 days.

(21) Appl. No.: 18/851,493

(22) PCT Filed: Mar. 30, 2023

(86) PCT No.: PCT/IB2023/053179

§ 371 (c)(1),
(2) Date: Sep. 26, 2024

(87) PCT Pub. No.: WO2023/187700

PCT Pub. Date: Oct. 5, 2023

(65) Prior Publication Data

US 2025/0223472 A1 Jul. 10, 2025

(30) Foreign Application Priority Data

Apr. 1, 2022 (IT) ........................ 102022000006521
Oct. 4, 2022 (IT) .......................... 10202200020373

(51) Int. Cl.

| | |
|---|---|
| ***C09J 123/20*** | (2006.01) |
| ***A61L 15/58*** | (2006.01) |
| ***B32B 3/26*** | (2006.01) |
| ***B32B 5/02*** | (2006.01) |
| ***B32B 7/12*** | (2006.01) |
| ***C09J 11/08*** | (2006.01) |

(52) U.S. Cl.

CPC ........... *C09J 123/20* (2013.01); *A61L 15/585* (2013.01); *B32B 3/26* (2013.01); *B32B 3/266* (2013.01); *B32B 5/02* (2013.01); *B32B 5/022* (2013.01); *B32B 7/12* (2013.01); *C09J 11/08* (2013.01); *B32B 2255/26* (2013.01); *B32B 2270/00* (2013.01); *B32B 2307/718* (2013.01); *B32B 2307/734* (2013.01); *B32B 2307/748* (2013.01); *B32B 2439/00* (2013.01); *B32B 2479/00* (2013.01); *B32B 2535/00* (2013.01); *B32B 2555/00* (2013.01); *B32B 2555/02* (2013.01)

(58) Field of Classification Search

CPC ........ C09J 2491/00; C09J 11/06; C09J 11/08; C09J 123/20; C09J 7/35; C09J 7/21; C09J 2301/312; C09J 2301/408; C08L 23/20; C08L 2205/025; C08L 2205/03; C08L 2207/10; A61L 15/585; B32B 3/26; B32B 3/266; B32B 5/02; B32B 5/022; B32B 7/12; B32B 2255/26; B32B 2270/00; B32B 2307/718; B32B 2307/734; B32B 2307/748; B32B 2535/00; B32B 2555/00; B32B 2555/02

USPC ........... 442/59; 156/334; 524/274, 342, 352, 524/401, 427, 430, 433, 435, 437, 445, 524/451, 452

See application file for complete search history.

(56) References Cited

U.S. PATENT DOCUMENTS

| | | | | |
|---|---|---|---|---|
| 3,900,361 A * | 8/1975 | Hoppe | .................. | C09J 123/20 524/427 |
| 4,568,713 A | 2/1986 | Hansen et al. | | |
| 4,937,138 A | 6/1990 | Mostert | | |
| 5,256,717 A | 10/1993 | Stauffer et al. | | |
| 5,786,418 A | 7/1998 | Strelow et al. | | |

FOREIGN PATENT DOCUMENTS

| | | |
|---|---|---|
| EP | 0314495 A2 | 5/1989 |
| EP | 3266824 A1 | 1/2018 |
| EP | 3266825 A1 | 1/2018 |
| EP | 3858933 A1 | 8/2021 |
| WO | 2018007451 A1 | 1/2018 |

OTHER PUBLICATIONS

Jenkins, et al., "Glossary of Basic Terms in Polymer Science", Pure and Applied Chemistry, (1996), vol. 68, No. 12, pp. 2287-2311.

(Continued)

*Primary Examiner* — Camie S Thompson
(74) *Attorney, Agent, or Firm* — Chrisman Gallo Tochtrop LLC

(57) ABSTRACT

Hot-melt adhesives are disclosed that include, a polymeric blend of two polymers of butene-1, A) and B). Polymer A) is a copolymer of non-isotactic butene-1, having a monomodal composition, a Polydispersity Index Mw/Mn not lower than 3.5, composed by butene-1 copolymerised with one or more alpha-olefin(s) selected from ethene, propene and alpha-olefins C5 to C12. Said polymer A) has a content of copolymerised comonomer(s) not lower than 20 mol %. Polymer B) is polymeric composition of isotactic butene-1, with Polydispersity Index Mw/Mn lower than 3.5 and a bimodal composition, i.e., constituted by two butene-1 polymers, B1) and B2), being homopolymers or copolymers of butene-1 with the same other alpha-olefins mentioned for polymer A), the overall content of comonomer(s) in B) being lower than 20% by mole. Both polymers A) and B) exhibit peculiar thermal properties, like Enthalpy of Fusion, Peak Melting Temperature and Glass Transition Temperature.

44 Claims, No Drawings

(56) References Cited

OTHER PUBLICATIONS

Choi et al., "Time dependent crystallinity of polybutene-1", Polymer Engineering and Science, (Oct. 1966), vol. 6, pp. 349-352 (Abstract Only).
Xin et al., "Polymorphic Behavior and Phase Transition of Poly(1-Butene) and its Copolymers", Polymers, (May 2018), vol. 10, No. 5, p. 556.
International Search Report in corresponding application PCT/IB2023/053179 dated Jun. 30, 2023.

* cited by examiner

HOT-MELT ADHESIVES COMPRISING BUTENE-1 POLYMERS AND SHOWING PECULIAR THERMAL CHARACTERISTICS

FIELD OF THE INVENTION

The present invention discloses new hot-melt adhesive formulations that comprise, as their main polymeric component, a blend of at least two polymers of butene-1. Said at least two polymers are different one from the other at least in some properties that first of all (but not only) are related with their most important thermal properties. In particular, the present hot-melt adhesives comprise a polymeric blend that is formed by at least two polymers of butene-1, A) and B), mixed in suitable and balanced ratios, said polymers being characterised by the following properties:

A) polymer A) is a non-isotactic copolymer of butene-1 having a monomodal composition, a Polydispersity Index Mw/Mn not lower than 3.5 and it is composed by butene-1 copolymerised with one or more alpha-olefin(s) selected from ethene, propene and the alpha-olefins from C5 to C12. Said polymer A) has a content of copolymerised comonomer(s) not lower than 20% by mole and it is further characterised by the following thermal properties, that are measured by DSC after five days of aging at room conditions (23° C. and 50% relative humidity):
  - an Enthalpy of Fusion not greater than 40 J/g, preferably not greater than 35 J/g and more preferably not greater than 30 J/g;
  - a Peak Melting Temperature not higher than 80° C.;
  - a Glass Transition Temperature not greater than −10° C.;

B) polymer B) is a polymeric composition of isotactic butene-1, with a global Polydispersity Index Mw/Mn lower than 3.5, and that has a bimodal composition. In fact it is in turn formed by two polymers of butene-1, B1) and B2), each having a single Polydispersity Index Mw/Mn lower than 3.5, and that are described in more details below. Said polymeric composition of isotactic butene-1 has a global content of copolymerised comonomer(s) lower than 20% by mole; and said comonomer(s) is (are) selected from ethene, propene and alpha-olefins having a number of Carbon atoms equal or greater than five. Moreover said polymeric composition of isotactic butene-1 is characterised by the following thermal properties, that are measured by DSC after five days of aging at room conditions:
  - an Enthalpy of Fusion greater than 20 J/g, preferably greater than 25 J/g and more preferably greater than 30 J/g;
  - a Peak Melting Temperature higher than 90° C.;
  - a Glass Transition Temperature not greater than −20° C.

Said polymeric compositions of isotactic butene-1 B), with a bimodal composition, can be produced both during the polymerisation step, inside the production reactor itself, in two steps of synthesis that are separated and distinct; or on the contrary, they can be also produced through a mechanical blending, at a sub-microscopic scale, of two polymers of butene-1 that have been synthesised separately and that are later intimately blended in the molten or in the solution state.

In a further embodiment of the present invention, the hot-melt adhesives disclosed herein comprise from 5% to 99.5% by weight of polymers, and preferably from 60% to 99.5% by weight of polymers.

In another embodiment, the present hot-melt adhesives comprise no more than 35% by weight, preferably no more than 25% by weight and even more preferably no more than 15% by weight, of components at low molecular weight, and in particular of the sum of tackifying resins plus viscosity modifiers plus waxes. As an example, most of these low molecular weight components have an average number Molecular weight, Mn, that typically is not greater than 2,500 g/mole, usually is not greater than 1,500 g/mole and often is below 1,000 g/mole.

In a third embodiment, the weight ratio between polymer A), i.e. the non-isotactic copolymer of butene-1, having a monomodal composition and a Polydispersity Index not lower than 3.5, and polymer B), i.e. the isotactic polymeric composition of butene-1, having a bimodal composition and a Polydispersity Index lower than 3.5, is greater than 1. Said combination between isotactic and non-isotactic polymers of butene-1, with different Polydispersity Indexes, different global content of comonomers and different thermal properties, provides new hot-melt adhesives an unexpected combination of strong adhesiveness, even on substrates that are difficult to be adhered, as e.g. plastic films, united with high cohesion and mechanical properties, especially after an aging of these adhesives in the solid state.

The hot-melt adhesives according to the present invention, further exhibit an excellent processability, even on industrial lines running at high or very high speed, for example equal or greater than 200 m/minute, as are the industrial lines used for the manufacturing of absorbent hygienic articles.

Definitions

The expressions “comprising” or “that comprise(s)” are used herein as open-ended terms, that specify the presence of what in the text follows said terms, but that does not preclude the presence of other ingredients or features, e.g. elements, steps, components, either known in the art or disclosed herein.

The expression “polymer(s)” is used herein according to the definition given in the document issued by ECHA—European Chemical Agency—December 2017 edition—and titled “How to decide whether a substance is a polymer or not and how to proceed with the relevant registration”. Hence, in the present invention we define as a “polymer” any chemical substance that contains more than 50% by weight of “polymeric molecules”; where said “polymeric molecules” are in turn defined as those molecules that contain at least three base units (monomeric ones or more complex) that are bound to a fourth unit, that can be equal or different from the first units. Therefore, said polymeric molecules contain in total at least four base units, that can be monomeric units or more complex ones (when e.g. the base unit is, in its turn, composed by two or more monomers as it happens in condensation polymers). The expression “polymer(s)” comprises both polymeric molecules formed by just one type of base units/monomer (homopolymer) as well as by multiple different types (copolymer).

In a similar way, the expression “oligomer(s)” means herein a chemical substance that contains more than 50% by weight of “oligomeric molecules”; where said “oligomeric molecules” contain less than three base units (monomeric ones or more complex) bound to another unit that can be equal or different from the first units. Also the expression “oligomer(s)” comprises both oligomeric molecules formed by just one type of base units/monomer (homo-oligomer) as well as by multiple different types (co-oligomer).

More specifically, the expression "homopolymer(s)" is used herein according to the definition given by IUPAC (International Union of Pure and Applied Chemistry) in the article "GLOSSARY OF BASIC TERMS IN POLYMER SCIENCE", published in "Pure and Applied Chemistry", Vol. 68, No. 12, pp. 2287-2311, 1996. Therefore, the expression "homopolymer(s)" means herein a polymer that is synthesised from just one type of monomer. Still according to the same reference, the expression "copolymer(s)" means in the present invention (unless a different meaning is specifically indicated) not only a polymer in the chemical composition of which two different monomers are used, but also polymers in the chemical composition of which three, four, five or more different monomers are used. According to the above mentioned reference, when one wants to emphasise the number of different comonomers that form a certain copolymer, one can also use, as an alternative, the expressions "bipolymer", "terpolymer", "quaterpolymer" and so on.

"Polydispersity Index" or "Molecular Weights Distribution Index" or "PDI" refers to a measure of the distribution of the molecular weight in a certain polymer. It is defined as the ratio between the weight average molecular weight Mw, and the number average molecular weight Mn:PDI=Mw/Mn. Greater values of PDI correspond to broader distribution curves of molecular weights and vice versa. Mw, Mn and therefore their ratio Mw/Mn=PDI, are measurable e.g. by Gel Permeation Chromatography (GPC).

The expression "bimodal composition", referred to a polymeric composition, means that said composition is formed by two polymers, that are mutually compatible and that are intimately dispersed one into the other at a sub-microscopic scale; said polymers are different in their average molecular weight and/or in their chemical composition and/or in both these properties. Said polymeric compositions, having a bimodal composition, can be made both during the polymerisation step, inside the production reactor itself, in two steps of synthesis that are separate and distinct; or on the contrary, they can be also produced through a mechanical blending, at a sub-microscopic scale, of two polymers that have been synthesised separately and that are later intimately blended in the molten or in the solution state.

The Enthalpy of Fusion, the enthalpy of Crystallisation and the Glass Transition Temperature of a certain material, are herein measured by Differential Scanning Calorimetry (DSC), according to the standard Methods ASTM D3417-99 and ASTM D3418-12. For measuring all these parameters, a rate of temperature change equal to 10° C./minute is herein always used.

When, for a certain material, the DSC Fusion or Crystallisation diagrams show two or more peaks (in case even partially overlapped), it is herein defined as the "Peak Melting Temperature" of that material or as the "Peak Crystallisation Temperature" of that material, the Peak Temperature of the peak that has the greatest area, and hence has the greatest Enthalpy.

"Room temperature", if not specifically defined in a different way, means a temperature equal to 23° C.; and "room conditions" means the conditions of an environment at a controlled temperature and relative humidity, at 23° C. and 50% relative humidity.

Because a few materials, used in the present invention, change some of their properties (e.g. the quantity and morphology of their crystalline fraction, and hence their Enthalpies of Fusion and their mechanical properties) as a function of the time elapsed from the moment of their solidification from the molten state, in the present invention we distinguish said properties that can change with time, between "Properties at Time Zero" and "Aged Properties" at a certain number of hours or days of aging, typically five days, after the material's solidification from the molten state.

Therefore a certain property "at Time Zero" (for example, an Enthalpy of Fusion at Time Zero), that may be also called as an "initial" property, or a property "in the initial conditions", means that said property is measured at 23° C. (unless that a different temperature is specifically indicated) and at 50% relative humidity, and at a time that is not longer than 120 minutes from the solidification of the material under test from the molten state.

On the contrary, a certain property that is e.g., "aged at five days" or "at five days" or "in aged conditions", means that said property is measured at 23° C. (unless that a different temperature is specifically indicated) and at 50% relative humidity, after five days from the solidification from the molten state of the material under test. During these five days of aging the material under test is kept in a climatised room, at 23° C. and 50% relative humidity.

The expressions "that is (are) not solid" are used herein to mean that a specific compound or material or ingredient or their blends, are in a physical state in which, even if they have a well definite volume, they do not have a fixed own shape, and they take the shape of the containers that contain them. Even in the case that they are sufficiently viscous to be temporarily shaped by themselves in any tridimensional shape, after being left at rest and without any external stress, apart from their own weight, they spontaneously flow and permanently deform, so to lose rather quickly (typically in a period of time that may range between a few seconds and about one day) their initial shape, taking the shape of the containers that contain them (if these ones were not already full to the brim) or of the solid surface on which they are lying. Therefore, this definition comprises all the materials that not only may be defined as "liquid" (both at high and low viscosity) according to the common meaning of this adjective, but also all those materials that, in the common language, are for example defined as "creamy", "pasty", "jelly-like", "fluid", "greasy", "semi-solid" and the like. A further way of defining in rheological terms what, in the present invention, is meant when a certain compound or material or ingredient or their blends are said to be "not solid" at room temperature, i.e. conventionally at the temperature of 23° C., is also by specifying that said "not solid" matters can be defined as "rheologically liquid", i.e. as defined in Rheology, that they, at the specified temperature of 23° C., have a Viscous Modulus G" that is higher than their Elastic Modulus G', or also, what is equivalent by definition, that their Tan Delta is greater than 1.

The equivalent expressions "Rheological Setting Point" or "Rheological Setting Temperature" or "Temperature of Rheological Setting" or "Temperature of the Crossing of the Moduli" or also "Crossover Point" and its symbol Tx, mean, in a rheological diagram in which are measured, as a function of temperature, the Elastic Modulus G', the Viscous Modulus G" and their ratio Tan Delta, the temperature at which the two Moduli cross (and in which therefore the value of Tan Delta is equal to 1) in the field of temperatures above room temperature. It indicates the temperatures at which the material under test melts or solidifies, in a rheological sense, passing from a molten state to a solid state or vice versa.

"Absorbent hygienic articles" refer to devices and/or methods concerning disposable absorbing and non-absorbing articles, that comprise diapers and undergarments for incontinent adults, baby diapers and bibs, training pants, infant and toddler care wipes, feminine catamenial pads, interlabial pads, panty liners, pessaries, sanitary napkins, tampons and tampon applicators, wound dressing products, absorbent care mats, detergent wipes, and the like.

"Perforated films" refers to films, typically made of plastic materials, like polyethene, that are perforated with multiple holes, and that can have both a bidimensional and a tridimensional structure, and with a typical hole size in the range between a few hundreds microns to about one millimeter, that are often used as components in absorbent hygienic articles.

"Fibrous substrates" refers to products having an essentially planar structure, formed by natural or synthetic fibers or their blends, both in the form of woven and of nonwoven fabrics, equally used as components in absorbent hygienic articles.

"Open Time" of an adhesive refers, especially for a hot-melt adhesive, to the interval of time during which, after its application from the melt on a first substrate, the adhesive is able to form sufficiently strong adhesive bonds for the intended use, with a second substrate that is brought into contact under moderate pressure with the first one. It is apparent that too short open times may make difficult-to-manage the application of an adhesive and the formation of sufficiently strong bonds. The open time of a holt-melt adhesive may be measured according to the test method ASTM D 4497-94, with the following conditions for the hot-melt adhesives disclosed herein:

Coating temperature of the adhesive film: 170° C.

Thickness of the adhesive film: 1 mm.

"Ring & Ball Softening Point" refers to the softening temperature of a material, measured according to the Method ASTM D 36-95.

Just for waxes, the "Softening Point" (called also "Dropping Point") is measured according to the Method ASTM D 3954-94.

The "Needle Penetration" of an adhesive is a measure of its softness. It is generally expressed as tenths of millimeter, dmm, and it is herein measured at 55° C., according to the Method ASTM D1321-04.

The dynamic viscosity of a molten or liquid material at a certain temperature is expressed as mPa·s and it is measured according to the Method ASTM D 3236-88.

The Melt Flow rate (MFR) of a polymeric material is expressed as g/10 minutes, and it is measured, at 190° C. and under a weight of 2.16 kg, according to the method ISO 1133-1.

The tack of a certain adhesive is herein measured according to the method ASTM D6195-03.

The overall Adhesive Strength or "Peel Strength" is defined as the average strength per unit of width needed to separate two substrates, bonded by the adhesive under test, measured through a separation test made at a controlled and constant speed, and under a controlled and constant debonding angle. It is herein measured according to the Method ASTM D 1876-01, separating the two substrates under a debonding angle of 180 degrees, by applying a separation speed of the two substrates equal to 150 mm/minute, that means that the testing dynamometer is actually moving at a speed of 300 mm/minute. The two substrates used herein are a polyethene film, with a basis weight of 23 g/m$^2$, supplied by Poligof (Italy), on which the molten adhesive at 165° C. is directly applied by slot-die extrusion at a basis-weight of 1.5 g/m$^2$, on a pilot line running at the very high speed of 250 m/minute, and on which a spunbonded polypropene nonwoven, with a basis weight of 12 g/m$^2$, supplied by Union Industries (Italy), is immediately bonded. The laminate structure formed by the glued plastic film and the nonwoven is then aged and conditioned for five days at 23° C. and 50% relative humidity. After this aging, the bonded laminate is tested for its Peel Strength according to the Method ASTM D 1876-01, by cutting from it the necessary samples in the number of six samples to be tested for each measurement. In each test, the measurement of the Peel Strength is made by recording the average strength in Newtons (N) needed to separate the two bonded substrates on a width of 50 mm; and after the six tests for each adhesive, its Peel Strength is calculated as the average value of the strengths recorded in its six tests.

The "Tensile Properties" or "Mechanical Properties in Tension" of all the materials disclosed herein, e.g. the hot-melt formulations, like the so called "Stress-Strain Curve", and the respective "Peak Stress" or "Ultimate Tensile Strength"; the "Stress at Break"; and "Elongation at Break" etc., are herein measured at 23° C. and 50% Relative Humidity (unless differently specified), according to the following method. For each material under test, a film is extruded at 170° C. with a thickness of 0.5 mm. From the extruded film, five rectangular samples are cut, with a length of 25 mm and a width of 6 mm. The samples, if this is required by the type of test, are aged for five days at 23° C. and 50% Relative Humidity. For assessing its Stress-Strain to break curve, each sample is fixed with clamps, at its narrowest ends, to the shafts of a Rheometer Ares G2, available from TA Instruments, equipped for Tensile tests with the so called "Torsion Rectangular" geometry. The free length of the sample is 10 mm. The mobile upper shaft, that has a maximum further run of 60 mm (hence corresponding to a maximum readable strain of 600%), is started at an extension rate equal to 6 mm/minute. These test conditions hence correspond to a Strain Rate of the sample equal to 0.1 s$^{-1}$, i.e. a frequency of 0.1 Hz. The tensile test is stopped either when the sample is fractured or when the rheometer has reached the maximum readable strain, equal to 600%. For each Stress-Strain to break curve, the rheometer measures the maximum "Peak Stress" or "Ultimate Tensile Strength", the maximum Strain and it also calculates the area under the curve itself, area that is equal to the Toughness of the material, expressed in J/m$^3$.

The rheological properties of a material, for example a polymer or an adhesive formulations, are herein measured by using a Rheometer Ares G2, available from TA Instruments. For the rheological properties "at Time zero" measured at decreasing temperature, the sample is melted between the rheometer's plates by increasing the temperature to 150° C. and conditioning the molten material at this temperature for 600 seconds. After this, the rheological test is started, under the strain frequency of 1 Hz, and by decreasing the temperature at the speed of 2° C./minute, until the sample reaches the temperature of −20° C., at which temperature the test is stopped.

For the rheological properties that vice versa are measured under conditions of increasing temperature, the following conditions for the test are used. If said properties are "at Time Zero", the test follows the same procedure described in the previous paragraph for the test in decreasing temperature. However, when the sample has reached the temperature of −20° C., it is conditioned at this temperature for 600 seconds; then the test is re-started by increasing the temperature at a ramp equal to 2° C./minute, at the frequency of 1 Hz, until the final temperature of 150° C. is reached.

However, when one wants to measure, in increasing temperature, the rheological properties, aged at five days, the following procedure is used: the sample is melted at 150° C.

between the rheometer's plates, and it is conditioned at this temperature for 600 seconds. Then, without doing any measurement, the sample is cooled—still positioned between the rheometer's plates—to the temperature of 23° C. The whole system is left for five days at the temperature of 23° C. and 50% relative humidity. When the aging time of five days has elapsed, the sample is further cooled to −20° C. and is conditioned at this temperature for 600 seconds. After this, the measurement is started, at the frequency of 1 Hz, and by increasing the temperature at the speed of 2° C./minute, until that final temperature of 150° C. is reached, and the test is stopped.

Other less usual parameters, measured according to specific methods, will be defined in the following pages, together with the detailed description of their measurement methods.

BACKGROUND

From a historical standpoint, the isotactic butene-1 homopolymers and copolymers have been industrially manufactured and sold, since 1964, by Companies like Huls, Mobil, Witco, but mainly by Shell, that since 1977 has been the main worldwide supplier. The production of such polymers and polymer grades have been later transferred to the Company LyondellBasell.

All the isotactic polybutenes-1 of "old generation" and their copolymers have been manufactured by using Ziegler-Natta catalysts, that produce polymers having very high Polydispersity Indexes, generally greater than 4 and often even greater than 6. Therefore, these polybutenes-1 show, inside the same polymer, a very wide distribution of molecular weights, with large fractions formed by very high and very low molecular weights. In fact, in the Ziegler-Natta processes, for obtaining a final average molecular weight that is sufficiently high, in order to give the polymer acceptable mechanical properties, it is therefore necessary (if e.g. Mw/Mn is equal or greater than 4) to synthesise a large fraction of polymeric chains with very high molecular weights. Hence, these "old generation" isotactic polybutenes-1 show also a high or very high viscosity in the molten state.

Moreover, since its discovery in 1954 by the Nobel Prize Giulio Natta, it has been realised that isotactic polybutene-1 and its copolymers show a very peculiar behaviour for what concerns their crystallisation after the solidification from the molten state. In fact, while all the other main polyolefins that can crystallise, like polyethene or polypropene, reach their final crystalline structure and percent of crystallinity, in a very quick way and often in an almost instantaneous way, the isotactic polybutene-1 crystallises in a very different way, that is often defined as a "delayed crystallisation" over long times. This crystallisation, delayed in time, is a quite complex phenomenon, given also the crystalline polymorphism of isotactic polybutene-1; and because of this phenomenon, after the solidification of the polymer from the molten state, not only its crystallinity level grows slowly with time, but there is also a slow transformation from the initial metastable crystalline form (called Crystalline Form II) into the stable crystalline form (called Crystalline Form I). This phenomenon, that causes an evolution with time of the crystallinity of solid isotactic polybutene-1, both in a quantitative and in a qualitative manner, occurs also at room conditions and is typically completed in a time frame comprised between three and seven days, on average in five days. This peculiar behaviour in crystallisation of isotactic polybutene-1, is e.g. described in the articles "Time dependent crystallinity of polybutene-1" by Choi and coworkers, published in Polymer Engineering and Science, Volume 6, Issue 4, October 1966 Pages 349-352, and "Polymorphic Behavior and Phase Transition of Poly(1-Butene) and its Copolymers" by Xin and coworkers, published in Polymers; 10(5):556, May 2018.

The previously mentioned characteristics of high molecular weight and of high melt viscosities of the "old generation" isotactic polybutenes-1, with a Polydispersity Index greater than 4, have often obliged people who tried to use these polymers as base-polymers for hot-melt adhesives, starting from Shell itself, to formulate adhesives that (in order to be easily processable) contain relatively low quantities of polybutene-1; and that therefore contain significantly greater percentages of the other typical ingredients of a hot-melt adhesive, ingredients that have low or very low molecular weights, e.g. with Mn often well below 2,500 g/mole, like tackifiers, viscosity modifiers and waxes.

For example, in the Shell U.S. Pat. No. 4,937,138, the inventors claim hot-melt adhesives that contain between 5% and 50% of polymers based on butene-1, formulated with as much as from 50% to 95% of a tackifier, and optionally also up to 60 parts for every 100 parts of the blend polymer plus tackifier, of additional components at low molecular weight, like viscosity modifiers or waxes. Unfortunately, this patent does not reveal the viscosities of the formulations of the Examples according to the invention. However, another rather similar patent by Shell, U.S. Pat. No. 4,568,713, shows in Table II that hot-melt adhesives, that contain 50% by weight of homopolymers of butene-1 or of copolymers between butene-1 and various levels of ethene, have anyhow very high viscosities, comprised between 20,000 and 25,000 mPa·s at the temperature of as much as 177° C., with a very difficult and unsatisfactory processability.

In a similar way, U.S. Pat. No. 5,256,717 shows, in Table 1, three formulations that, for having reasonable viscosities still at as much as 177° C. (350 F), contain as little as 20% by weight of a Ziegler-Natta copolymer between butene-1 and ethene, Duraflex 8910, blended with as much as 80% by weight of a tackifier and of a viscosity modifier.

Also U.S. Pat. No. 5,786,418 for example, while it claims in claim 1) content of polybutene-1 between 10% and 60% by weight, actually in Column 2, lines 23 to 34, states that the scope of the invention is to disclose a preferred adhesive formulation that contains only 25% by weight of polymer, said polymer being a copolymer between butene-1 and ethene, and as much as 75% by weight of ingredients at low molecular weight, like tackifiers and viscosity modifiers.

Even when the Prior Art has shown Examples of hot-melt adhesives that contain relatively high quantities (e.g. 50% by weight or more) of these butene-1 polymers, synthesized with Ziegler-Natta catalysts and having therefore a Polydispersity Index greater than 4 and large fractions of high or very high molecular weights, the results have been that said formulations have generally showed so high viscosities in the molten state that their processability is extremely poor and difficult, especially on industrial lines running at high speed, like 200 m/minute or even greater. Beside the already mentioned U.S. Pat. No. 4,568,713, one can also consider EP 0 314 495 A2, a document that, in its tables 1 and 2, shows seven examples according to the invention and four comparative examples. All these examples contain 50% by weight of various homopolymers or copolymers of butene-1, all of them synthesised with Ziegler-Natta catalysts, the remaining 50% by weight of the formulation being a tackifier. EP 0 314 495 A2 does not disclose the viscosities of these adhesives shown in the examples. However, the inventors of the present invention have experimentally measured the melt viscosity of Example 2, according to the invention, in table 2 of EP 0 314 495 A2 and have found a value of as much as 50,200 mPa·s at 170° C. and of 36,300 mPa·s at 177° C. These viscosities are so unusually high for a hot-melt adhesive that it's practically impossible to process these hot-melt formulations not only on industrial lines at high speed, like 200 m/minute and higher, but also on lines running at much lower speeds; and in any case these very viscous adhesives are processable with extreme difficulty even on lines operated at unacceptably low speeds, like for example 5 m/minute.

The need to formulate said old-generation polybutenes-1, synthesised with Ziegler-Natta catalysts, and having a very high Polydispersity Index, typically greater than 4, causes various problems if, in order to obtain adhesive formulations at sufficiently low viscosity, one is obliged to formulate adhesives with a particularly low content of polymers and hence with a much higher and prevailing content of components at low molecular weight, like typically tackifiers, viscosity modifiers and waxes. In fact, said ingredients at low molecular weight, tend to demix with time and to migrate out of the formulations that contain high percentages of said light ingredients, which finally bleed out of the adhesive's surface. These phenomena have very negative consequences, starting from the fact that this causes an unacceptable change and deterioration with time of the properties of the adhesive itself. Moreover, this molecular migration and this bleeding on the adhesive's surface of the components at low molecular weight, cause the generation of malodours and also, if these bled substances come in contact with the skin of a user, they can cause serious problems of skin irritation, sensitisation, allergic and even toxic effects.

Besides these highly negative and unacceptable phenomena, even more when the adhesives are used inside medical articles and inside absorbent hygienic articles, when we consider hot-melt adhesives based on butene-1 polymers, a too low content of the polymeric fraction has a strongly negative influence also on the peculiar "crystallisation delayed in time" showed by polybutene-1 and its copolymers. In fact, the excessive "dilution" of the fraction formed by butene-1 polymers having a high Polydispersity Index, can lead to further negative effects that affect the crystallisation of said polymers. For example:

- the dilution itself of the polymeric chains causes non only a slow-down in their crystallisation, but even more this may lead to a worsening of the "quality" of the formed crystallinity itself, because, at an equal level of final crystallinity, in a more dilute environment it's statistically more probable the formation of more numerous crystals that are however, smaller and "weaker", more dispersed inside the mass of the adhesive;
- one can reasonably think that the exclusive use of butene-1 polymers having a high Polydispersity Index, owing to the presence of a massive fraction of polymeric chains at very low molecular weight (each of which chains can act as a nucleating agent/starter of crystallisation) can even more lead to the formation, in a practically uncontrolled way, of very numerous crystals that are however, on average, smaller, weaker and less "perfect".
- even the presence of substantial fractions of high and very high molecular weight, in hot-melt adhesives containing only butene-1 polymers with high Polydispersity Indexes, has significant negative influences on the quality and quantity of the final crystalline phase that it's possible to obtain. In fact, as it is well known in Polymer Science, the level of final crystallinity and the "quality/perfection" of crystals that can be obtained in the crystallisation of a polymer, are inversely proportional to the average molecular weight of the polymer itself; and these characteristics decrease/worsen with an increase in the average molecular weight of the same polymer as e.g. clearly illustrated in the book "Crystallization of Polymers", edited by Marcele Dosiere, page 26 and the following ones.

However, it is necessary to notice that the presence of said significant fractions of very low and very high molecular weights in hot-melt adhesives containing only polybutenes-1, having high Polydispersity Indexes, has also some positive effects on a few important properties of said hot-melt adhesives. In fact, as it is well known to every person having an average expertise in the Science of Hot-Melt Adhesives, if the average molecular weight of the contained polymers is kept constant, the presence of significant fractions of polymeric chains with a low or very low molecular weight leads to adhesives that show a greater adhesiveness; in particular, they show both a higher Tack and a higher Peel Strength. On the contrary, the fractions having high or very high molecular weight help to improve (of course, at equal polymer content in the adhesive and at equal average molecular weight of said polymer) the cohesion of the adhesive itself.

Therefore and concluding, the Prior Art does not teach how to formulate hot-melt adhesives, based on "old generation" Ziegler-Natta butene-1 polymers, that show a low melt viscosity and excellent and easy processability on industrial lines running at high speed, like 200 m/minute and more, combined also with the need of keeping a relatively low content of other, non-polymeric components/additives having low molecular weights, like tackifiers, viscosity modifiers and waxes. This latest need, as already illustrated, is aimed at avoiding the migration and the bleeding of these light additives, which phenomena may cause further very negative effects, like an unacceptable change of the main adhesive properties with time, the generation of malodours, possible allergic reactions and even toxic effects if these bled light components contact the skin of a user. All this, without however of course renouncing the beneficial effects that those polymeric fractions at very low and very high molecular weight have on the contrary on other fundamental properties for an adhesive, and especially on a good Tackiness and Peel Strength, combined with a sufficient cohesion.

SUMMARY OF THE INVENTION

The problem that the present invention aims at solving is to formulate hot-melt adhesives that have relatively low viscosities in the molten state and that can therefore be easily processed even on industrial lines running at high speed, like 200 m/minute and more; and that show an optimum balance between the main and essential properties of a hot-melt adhesive, and especially:

- a high adhesiveness, expressed in particular as a high Peel Strength;
- a relatively low content of ingredients at low molecular weight, like tackifiers, viscosity modifiers and waxes, This with the main scope of minimising problems like malodours, allergic or toxic effects for the users, because of the molecular migration and bleeding out of the adhesive of said light ingredients, if their content is too high;
- a qualitative and quantitative optimisation of the crystallisation delayed in time, typical of butene-1 polymers, with the aim of obtaining crystals that are as much as possible "robust", morphologically "perfect" and that therefore can give a strong cohesion and strong mechanical properties, even without the presence of too high molecular weights, that, on the contrary, are increasing too much the adhesive's melt viscosity.

Said problems are solved by a hot-melt adhesive having the features of claim 1), by a bonded structure having the features of claims 36) and 37), by articles having the features of claims from 38) to 44). The other sub-claims disclose preferred embodiments.

DETAILED DESCRIPTION OF THE PREFERRED EMBODIMENTS AND MAIN PROPERTIES OF THE ADHESIVES ACCORDING TO THE PRESENT INVENTION

The hot-melt adhesives disclosed in the present invention comprise, as their main component, a polymeric blend of two different types of polymers both based on butene-1. In particular, the present hot-melt adhesives comprise a polymeric blend formed by at least two polymers of butene-1, A) and B), blended in balanced and suitable ratios, said polymers being characterised by the following properties:

A) polymer A) is present in the blend at a level ranging between 5% by weight and 95% by weight. It is a non-isotactic copolymer of butene-1, having a monomodal composition, a Polydispersity Index Mw/Mn not lower than 3.5 and it is composed by butene-1 copolymerised with one or more alpha-olefins selected from ethene, propene and the alpha-olefins from C5 to C12. Said polymer A) has a content of copolymerised comonomer not lower than 20% by mole, and it is further characterised by the following thermal properties, measured after five days of aging at room conditions:
 - an Enthalpy of Fusion not greater than 40 J/g, preferably not greater than 35 J/g and more preferably not greater than 30 J/g;
 - a Peak Melting Temperature not higher than 80° C.;
 - a Glass Transition Temperature, measured by DSC, lower than −10° C.;

B) polymer B) is present in the blend at a level ranging between 95% by weight and 5% by weight. It is a polymeric composition of isotactic butene-1, having a bimodal composition and a global polydispersity Index Mw/Mn lower than 3.5. It is in turn further formed by two butene-1 polymers, B1) and B2). In particular said polymeric composition comprises:
 - B1) from 10% to 90% by weight of a butene-1 copolymer with one or more comonomers selected from ethene, propene and alpha-olefins with a number of Carbon atoms equal or greater than five, said copolymer B1) having a copolymerised comonomer(s) content lower than 20% by mole and a Polydispersity Index Mw/Mn lower than 3.5;
 - B2) from 90% to 10% by weight of a homopolymer of butene-1 or of a copolymer of butene-1 with one or more comonomers selected from ethene, propene and alpha-olefins with a number of Carbon atoms equal or greater than five, said homopolymer or copolymer B2) having a copolymerised comonomer(s) content not greater than 5% by mole, and a Polydispersity Index lower than 3.5.

Said polymeric composition of isotactic butene-1 is characterised by the following thermal properties, measured after five days of aging at room conditions:
 - an Enthalpy of Fusion greater than 20 J/g, preferably greater than 25 J/g and more preferably greater than 30 J/g;
 - a Peak Melting Temperature greater than 90° C.;
 - a Glass Transition Temperature, measured by DSC, not greater than −20° C.

Polymer A) has a viscosity at 190° C. comprised between 1,000 mPa·s and 200,000 mPa·s, while polymer B) has a viscosity at 190° C. comprised between 1,000 mPa·s and 300,000 mPa·s. Moreover, the polymeric composition of isotactic butene-1 B) has a ratio between its components B1) and B2) so that its overall content of comonomer (or comonomers) is lower than 20% by mole and it's preferably comprised between 3% and 18% by mole.

In a preferred embodiment, the polymeric blend, comprising the butene-1 polymers A) and B), has a ponderal ratio between A) and B) that is greater than 1.

In another embodiment, the polymeric blend, comprising the butene-1 polymers A) and B), comprises also from zero to 30% by weight, of a third butene-1 polymer C1). Said butene-1 polymer C1) can be a homopolymer or a copolymer; in this latest case in it butene-1 is copolymerised with one or more alpha-olefins selected from ethene, propene and alpha-olefins from C5 to C12. Said polymer C1) is also characterised by having a content of copolymerised comonomer (or of comonomers) lower than 20% by mole, a Polydispersity Index greater than 3.5, an Enthalpy of Fusion at five days of aging greater than 20 J/g; a Peak Melting Temperature, still at five days, greater than 80° C. and a Glass Transition Temperature, measured by DSC after five days of aging, not greater than −10° C.

In a third embodiment, alternative to the previous embodiment, the polymeric blend, comprising the butene-1 polymers A) and B), comprises also from zero to 30% by weight, of another butene-1 polymer C2). Said butene-1 polymer C2) can be a homopolymer or a copolymer; in this latest case in it butene-1 is copolymerised with one or more alpha-olefins selected from ethene, propene and alpha-olefins from C5 to C12. Moreover, said polymer C2) is also characterised by having a content of copolymerised comonomer (or of comonomers) not lower than 20% by mole, a Polydispersity Index lower than 3.5, an Enthalpy of Fusion at five days of aging not greater than 40 J/g; a Peak Melting Temperature, still at five days, not greater than 90° C. and a Glass Transition Temperature, measured by DSC after five days of aging, not greater than −20° C.

In a fourth embodiment, said butene-1 polymers C1) and C2) have a monomodal composition.

In a fifth embodiment, the overall polymeric blend, comprised in the hot-melt adhesives according to the present invention, comprises also from zero to 30% by weight of a polymer (i.e. a homopolymer or a copolymer) that does not contain butene-1. Preferably said polymer, that does not contain butene-1, is a polyolefin, and even more preferably said polyolefin is a homopolymer or a copolymer synthesised from one or more alpha-olefins selected from ethene, propene and alpha-olefins from C5 to C12.

In a sixth embodiment, the above mentioned polyolefin contains hexene.

In a seventh embodiment, said polymer in whose composition butene-1 is not present, is a copolymer between propene and ethene.

In an eighth embodiment said copolymer between propene and ethene has a heterophasic structure.

In general, the sum of all the polymers, that are present in the hot-melt adhesives according to the present invention, forms from 5% to 99.5% by weight of the adhesive itself or alternatively from 60% to 99.5% by weight.

More detailed information about the main polymeric components of the present hot-melt adhesives, and about further possible additional ingredients is given below.

The Polymeric Compositions of Isotactic Butene-1 with Low Polydispersity Index, Low Viscosity and with a Bimodal Composition The isotactic polymers based on butene-1, with high Polydispersity Index and synthesised with Ziegler-Natta catalysts, at high molecular weight and high viscosity in the molten state, have monopolised the market of polybutene-1 and of its copolymers for many years, and not only for uses in the field of adhesives. However recently a few Companies, that manufacture isotactic polybutene-1, have abandoned the classic Ziegler-Natta catalysts for new metallocene catalysts. These novel processes allow to synthesise polybutenes-1 of "new generation" that exhibit new and substantially improved characteristics, like average molecular weights that are significantly smaller and much better controlled (and therefore much lower melt viscosities), much smaller polydispersity Indexes Mw/Mn, all novel properties that give to these polymers improved characteristics, like excellent cohesion and strong mechanical properties even in the presence of relatively low melt viscosities.

Especially the Company LyondellBasell has begun to produce isotactic polymers of butene-1, synthesised with metallocenic catalysts, that show quite peculiar compositions and structures, as well as new and significantly improved properties, compared with all the previous isotactic butene-1 polymers of "old generation". These novel metallocenic butene-1 polymers are marketed under the trade mark Koattro PB M. In particular these new metallocenic polymers of isotactic butene-1, described e.g. in the patent applications EP 3266824 A1 and EP 3266825 A1, are polymeric compositions formed by two different isotactic polybutenes. They have therefore a bimodal composition, in the sense that the two constituent polymers may differ for their average molecular weights, or may differ for their chemical compositions, or may differ for both these characteristics. Said peculiar bimodal compositions of butene-1 based polymers may be obtained directly in two distinct and subsequent phases of polymerisation inside the same reactor; or alternatively they may be also obtained by mixing, at a sub-microscopic level, the two polymers that have been separately synthesised and that are later intimately blended in the molten state or as solutions.

Said metallocenic bimodal polymeric compositions of isotactic polybutene-1 have typically an overall average Number Molecular Weight not greater than 150,000 g/mole, preferably not greater than 100,000 g/mole and more preferably not greater than 80,000 g/mole.

These novel metallocenic and bimodal polymeric compositions of isotactic polybutene-1 have also a high Melt Flow Rate (and therefore have low melt viscosities) and a low overall Polydispersity Index, lower than 3.5 and often even lower than 2.5. They are typically formed by a first polymer B1) that is an isotactic copolymer of butene-1 with one or more comonomers selected from ethene, propene and alpha-olefins with a number of Carbon atoms equal or greater than five, and with a low content of comonomer that is not greater than 20% by mole; and by a second polymer B2) that is an isotactic homopolymer of butene-1 or an isotactic copolymer of butene-1 with one or more comonomers selected from ethene, propene and alpha-olefins with a number of Carbon atoms equal or greater than five, with an even lower content of comonomer ranging from zero to 5% by mole. The two polymers of butene-1 are present, inside the polymeric composition, in a mutual ratio such that the overall content of comonomer(s) in the composition is not greater than 20% by mole and preferably is comprised between 3% and 18% by mole.

This high content of butene-1 (mainly in its isotactic form), as well as the particularly low value of the Polydispersity Index, and therefore the absence of fractions having very low and very high molecular weights, causes not only melt viscosities that are on average significantly lower and hence a better processability (of course at equal average molecular weight of the polymer and at equal content of the same polymer in the adhesive formulation), but this causes also various other positive effects on the "delayed crystallisation" of polybutene-1 inside these peculiar novel polymeric compositions.

First of all the greater Melt Flow Rate, compared with the previous isotactic polybutenes, MFR that is typically comprised between 40 g/10 minutes and 6,000 g/10 minutes, corresponding to a range of melt viscosities at 190° C. between about 1 Pa·s and 250 Pa·s, allows to formulate adhesives that are more "concentrated" in polymers, however still keeping relatively low viscosities and therefore excellent processability even on industrial lines running at high speed. This greater concentration of the isotactic polybutene, allows per se, to obtain crystals that are on average more robust and more "perfect".

Also, the very low Polydispersity Index of these bimodal metallocenic compositions of isotactic polybutene, and hence the absence of fractions at very low and very high molecular weights, gives further positive effects, useful for optimising the qualitative and quantitative development of the delayed crystallisation with time, for the molecules and the molecular segments of isotactic polybutene.

First of all, a low Polydispersity Index and hence a narrow distribution of the molecular weights, means that all the molecules of a certain polymer have molecular weights that are "more similar" among them, compared to other polymers having greater Polydispersity Indexes; and it is well known to all persons that have an average knowledge in the science of Polymers, that the crystallisation of a certain polymeric matrix occurs in the easier way, i.e, that the formed crystals are more numerous and qualitatively more "perfect", the more the molecular characteristics of the various chains of that polymer are similar for what concerns their structure, composition, molecular weight (better if not too high) and so on.

Besides this, as already illustrated in part above, the absence of fractions at very low and very high molecular weights, in these novel, metallocenic and bimodal isotactic polymeric compositions of butene-1, has per se a positive influence on an optimum development with time, both in a qualitative and quantitative sense, of the delayed crystallisation of isotactic polybutene-1. In fact, for example, the substantial absence in these peculiar new polymers of chains at very low molecular weight, each of which may act as a nucleating agent and as a triggerer of crystallisation, removes the possibility that the crystallisation may start in a too quick or uncontrolled way, and that it may form an excessive quantity of crystals that, at equal overall level of crystallisable molecules and of final achievable level of crystallinity, will be on average smaller and less robust. Or also, said in a different way, the substantial absence in these polymeric compositions, of too low molecular weights, in the fraction of isotactic polybutene-1 that can crystallise, and hence the absence of very a high number of possible nuclei/centres of crystallisation, allows (as it is clear to every person with an average knowledge of the Science of Polymers) in the hot-melt adhesives according to the present invention and that comprise such polymeric compositions of isotactic polybutene-1, the formation of crystals that on average are bigger, more robust and morphologically more "perfect" compared to what it can happen in similar adhesive formulations that on the contrary are based on isotactic polybutenes-1 of old generation, synthesised with Ziegler-Natta catalysts. This impinges also on a substantial improvement of the final properties, both adhesive and mechanical ones, of the hot-melt adhesive formulations disclosed in the present invention.

Therefore, the presence of a significantly smaller presence of "spontaneous crystallisation-centres", essentially formed by the chains of isotactic polybutene-1 at low and very low molecular weight, causes the fact that, in the present hot-melt adhesive formulations, the crystallisation of isotactic polybutene-1 takes place at a slower speed, with two main positive consequences. From one side, this slower and more controlled crystallisation tends to extend the "Open Time" of the adhesives disclosed herein, with advantageous consequences on the ease and effectiveness with which these adhesives are able to adhere on various substrates. Furthermore, as said and as well known to all persons who have an average knowledge of the science of polymers, a slower crystallisation favours the formation of crystals that are bigger, more robust and more morphologically "perfect", in this way hence further improving the characteristics both of adhesiveness and of mechanical strength/cohesion of the hot-melt adhesive formulations disclosed by the present invention.

Equally, it is also reasonable to believe that the practically full absence, in the present adhesive formulations, also of fractions at high and very high molecular weight (that on the contrary are massively present in the polybutenes-1 from Ziegler-Natta catalysts) has as well important positive consequences on the quality and quantity of the crystalline phase formed inside the present adhesives. For example, it is well known in the Science of Polymers, that the final "crystallinity level" that can be obtained in a polymer, as well as the "quality" of its crystals are inversely dependent on the average molecular weight of the polymer itself, as e.g., clearly explained at page 26 and following pages, book "Crystallization of Polymers" edited by Marcele Dosiere.

From all these considerations, it is possible to conclude that hot-melt adhesives that comprise the above described polymeric compositions of isotactic butene-1, with a bimodal composition and an overall Polydispersity Index lower than 3.5 and preferably even lower than 2.5, first of all show an optimum crystallisation, delayed in time, both in quantitative and qualitative terms, of the chains and segments formed by isotactic polybutene-1. In other words, inside these polymeric compositions of isotactic polybutene-1 a sufficiently slow crystallisation is occurring, that typically completes between three and seven days, on average in five days, at room conditions (i.e., at 23° C. and 50% relative humidity). During these days an increase of the number and of the size of the crystals takes place, that are also slowly transformed from the initial metastable "Form II", that forms at short times from the solidification from the molten state, into the final and stable form of isotactic polybutene-1, called "Form I", that has better mechanical and thermal properties.

This is made evident also by the thermal characteristics of these bimodal polymeric compositions of isotactic polybutene-1, that typically have, after five days of aging at room conditions, an Enthalpy of Fusion greater than 20 J/g, a Peak Melting Temperature higher than 90° C. and a Glass Transition Temperature, measured by DSC, not higher than −20° C. These thermal characteristics, and especially the first two properties, are clearly related with the formation of particularly robust and "perfect" crystals.

All these phenomena generate in the hot-melt adhesives that comprise such bimodal polymeric compositions isotactic polybutene-1, very positive properties like in particular an excellent processability, both in spraying and in slot-die coating/extrusion, even on industrial lines running at high speed, equal or greater than 200 m/minute. This is due to the low viscosity and to the narrow distribution of molecular weights, i.e., to the absence of high and very high molecular weights. Moreover, thanks also to the particularly robust and morphologically "perfect" structure of the crystals of isotactic polybutene-1, formed in the slow crystallisation delayed in time, excellent levels of cohesion are also achieved. Finally, because one can formulate these polymers with relatively low levels of other ingredients at low molecular weight, like tackifiers, viscosity modifiers or waxes, thanks to the lower viscosity of these new polymers, the present hot-melt adhesives exhibit an absence or a substantial decrease of the molecular migration and bleeding of these low molecular weight ingredients out of the formulation, and hence of the negative important effects that derive from said phenomena, like the generation of malodours and of allergenic or even toxic effects for the contact of the adhesives with the skin of a user.

Even considering hot-melt adhesives that comprise, as their main polymeric component, only the above illustrated bimodal polymeric compositions of isotactic butene-1, with a low overall Polydispersity Index Mw/Mn, these hot-melt adhesives have already for sure several very positive properties, like the ones mentioned above.

However, especially for certain more demanding uses, these already positive properties of hot-melts comprising just the above mentioned bimodal polymeric compositions of isotactic butene-1, may be not sufficient.

For example, one of the most typical and most industrially important uses in which hot-melt adhesives, that are based only on the above mentioned bimodal polymeric compositions of isotactic butene-1 with a low Mw/Mn, do not fully meet the most demanding requests of the users, is when said thermoplastic adhere substrates that are particularly adhesives must "difficult" to bond, like typically substrates made of plastics at low surface tension, as in particular polyolefinic films, both perforated and not; or nonwovens still made of polyolefins, as well as the combinations of such polyolefinic films bonded/laminated to polyolefinic nonwovens, a use that is quite often occurring e.g. in the manufacturing of absorbent hygienic articles like baby-diapers. In these uses in fact, it can happen that hot-melt adhesives that comprise only, as their main polymeric component, the above mentioned bimodal polymeric compositions of isotactic butene-1 with a low value of the overall Polydispersity Index, show (besides the indubitably positive characteristics already mentioned) also some deficiencies and insufficient performances for what concerns other properties. This is first of all true for what concerns an insufficient tackiness and adhesiveness (expressed e.g. as a Peel strength) on the above mentioned "difficult to bond" polyolefinic substrates. As already said, in fact, the absence of low and very low molecular weights may also negatively affect certain adhesive properties, like the tackiness and the Peel Strength, especially when it is required to achieve sufficiently strong adhesion on substrates having a very low surface tension (and that therefore are very difficult to be "wetted" and adhered by a hot-melt adhesives) as e.g. the plastic films and nonwovens made of polyolefins.

In order to solve this apparent contradiction, in a situation in which it is desired to keep at the maximum level the peculiar excellent properties given to the hot-melt adhesives by the mentioned bimodal polymeric compositions of isotactic butene-1, with a low Polydispersity Index lower than 3.5, without at the same time renouncing the optimum values of tackiness and adhesiveness, that in an adhesive are on the contrary typically generated by the presence also of some polymeric chains at low and very low molecular weight (e.g. typically comprised between 300 g/mole and 5,000 g/mole), the inventors of the present invention have surprisingly found that this unexpected combination of positive characteristics, i.e. a good processability, a low melt viscosity, and an excellent cohesion (all characteristics given by the bimodal polymeric compositions of isotactic butene-1 with Mw/Mn lower than 3.5) however combined with also a very good tackiness and adhesiveness even on difficult-to-bond substrates like polyolefinic films and nonwovens, can be achieved, in a fully unexpected way, by blending, inside the herein disclosed hot-melt adhesives, the mentioned bimodal polymeric compositions of isotactic butene-1, with Mw/Mn lower than 3.5, with different copolymers, still based on butene-1. These different copolymers of butene-1 are on the contrary non-isotactic, have a monomodal composition and also have a Polydispersity Index Mw/Mn that is not lower than 3.5, often is not lower than 4, and in various cases it is even not lower than 6; i.e. these copolymers, still based on butene-1, contain however also not-negligible fractions of low and very low molecular weights, for example comprised between 300 g/mole and 5,000 g/mole.

Said non isotactic and monomodal copolymers of butene-1, at high Polydispersity Index Mw/Mn, not only give to the present hot-melt adhesive formulations excellent values of Tackiness and Adhesiveness even on difficult-to-bond substrates, but, even more surprisingly, also improve the already good processability, even on lines running at high speed, especially for applications with slot-die extrusion and coating.

Therefore, the polymeric blends between the above mentioned bimodal polymeric compositions of isotactic butene-1, with a low Polydispersity Index Mw/Mn, typically lower than 3.5 (herein conventionally called “Polymer B”), and the also above described non-isotactic, monomodal copolymers of butene-1, having also a Polydispersity Index not lower than 3.5, often not lower than 4, and even not lower than 6 (herein conventionally called “Polymer A”), offer, in a fully unexpected and surprising way, a combination of the most positive properties typical of the two different types of polymers, both derived from butene-1. At the same time these blends surprisingly also cancel or anyhow decrease at substantially minor and even non-detectable levels, the negative characteristics of the said two types of butene-1 polymers, as e.g. the high melt viscosities and the poor cohesion that are typical of non-isotactic butene-1 polymers with high Mw/Mn, with significant fractions of very high and very low molecular weights.

The inventors have even more surprisingly found that, in said blends of the polymer A) with the polymer B), the optimisation of the positive properties of the two types of butene-1 polymers, while keeping at negligible levels their various negative characteristics, can be achieved in the best way even in hot-melt adhesives in which the ponderal ratio between polymer A) and B) is greater than 1, provided that said non isotactic and monomodal copolymers of butene-1, with a Polydispersity Index not lower than 3.5, further show characteristics that are illustrated in greater details in the following paragraph.

The Non-Isotactic Copolymers of Butene-1 with High Polydispersity Index and with a Monomodal Composition For being advantageously used in the above mentioned polymeric blend, on which the present hot-melt adhesives are based, blend that can comprise from 5% to 95% by weight of polymer A) with from 95% to 5% by weight of polymer B), these already partially described non isotactic monomodal copolymers of butene-1, with an Mw/Mn value not lower than 3.5, must be selected also according to the further characteristics illustrated below.

These copolymers, herein identified as Polymer A), are formed by butene-1 copolymerised, in a non-isotactic form, with one or more alpha-olefin(s) selected from ethene, propene and the alpha-olefins from C5 to C12. The synthesis may happen with any type of catalysts (for example with Ziegler-Natta catalysts), provided that the resulting copolymer does not have significant fractions of chains with an isotactic structure, and provided that it has a final Polydispersity Index Mw/Mn that is not lower than 3.5, and that preferably is even greater.

Their average molecular weights must be comprised inside a well-defined range that is not too high; more specifically, these non isotactic butene-1 copolymers have an average Number Molecular Weight Mn not greater than 30,000 g/mole and preferably not greater than 20,000 g/mole. With these average molecular weights, they generally show melt viscosities at 190° C. between 1 Pa·s and 200 Pa·s, but that preferably are substantially lower, e.g. comprised between 1 Pa·s and 50 Pa·s.

Differently from polymer B), i.e the polymeric composition of isotactic butene-1, with overall Mw/Mn lower than 3.5 and with a bimodal composition, these non-isotactic copolymers of butene-1, A), have a monomodal composition. Furthermore, while polymer B) comprises, in its chemical composition a prevailing quantity of butene-1, greater than 80% by mole, and preferably between 82% and 97% by mole, the non-isotactic and monomodal copolymers of butene-1, A), have significantly higher levels of comonomer(s), being said comonomer(s), that are copolymerised with butene-1, never lower than 20% by mole.

These non-isotactic and monomodal copolymers of butene-1, with high Polydispersity Index, are also characterised by the following thermal properties, measured after five days of aging at room conditions:

- an Enthalpy of Fusion not greater than 40 J/g;
- a Peak Melting Temperature not higher than 80° C.;
- a Glass Transition Temperature, measured by DSC, lower than −10° C.

These thermal properties, and in particular the first two properties, mean not only a substantial absence in these copolymers of segments of butene-1 that can crystallise with an isotactic structure, but indicate also a low quantity of overall crystallinity that may in case form, a low crystallinity that in any case is significantly different, both quantitatively and qualitatively, from the crystallinity that is formed inside the other butene-1 polymer B).

Copolymers of butene-1 with a monomodal composition and with a Polydispersity Index not lower than 3.5, that can be used in the present invention as the polymer A), in blend with polymer B), are for example manufactured and sold by Evonik with the trade mark Vestoplast and by Rextac with the trade mark Rextac.

As already previously mentioned, the polymeric fraction of the hot-melt adhesives disclosed in the present invention, may also comprise, besides polymer A) and polymer B), from zero to 30% by weight of further polymers that have been already described in the previous paragraphs.

The sum of all the polymers comprised in the hot-melt adhesives according to the present invention, constitutes from 5% by weight to 99.5% by weight of the hot-melt adhesive itself.

In a further embodiment, the sum of all the polymers comprised in the hot-melt adhesives according to the present invention, constitutes from 60% by weight to 99.5% by weight of the hot-melt adhesive.

Additional Ingredients

The present hot-melt adhesives may comprise also other additional ingredients. In particular:

Tackifiers

In an embodiment of the present invention, the adhesive formulations according to this invention also comprise from zero to 70% by weight of a tackifying resin or of a blend of tackifying resins. Said tackifier or blend of tackifiers has a Ring & Ball softening point comprised from 5° C. to 160° C. and preferably not lower than 70° C. It/they can be selected from: aliphatic hydrocarbon resins and their partially or totally hydrogenated derivatives; aromatic hydrocarbon resins and their partially or totally hydrogenated derivatives; aliphatic-aromatic hydrocarbon resins and their partially or totally hydrogenated derivatives; polyterpene resins and modified polyterpene resins and their partially or totally hydrogenated derivatives; rosins, their esters and their partially or totally hydrogenated derivatives. The hydrogenated tackifying resins, both aliphatic or aromatic or aliphatic-aromatic, are particularly preferred because they show an optimum compatibility with butene-1 polymers, both polymer A) and polymer B), that, as said, are the main components of the present adhesives.

Viscosity Modifiers that are not Solid at Room Temperature

In a second embodiment of the present invention, the hot-melt adhesives disclosed herein, also comprise from zero to 40% by weight of at least one viscosity modifier or of a blend of viscosity modifiers that is/are not solid at room temperature, i.e. at 23° C. Said viscosity modifier or blend of viscosity modifiers is/are selected from paraffinic mineral oils; naphthenic mineral oils; paraffinic and naphthenic hydrocarbons that are not solid at room temperature, and their blends; oligomers and polymers, not solid at room temperature, of polyolefins from C2 to C20, and their co-oligomers and copolymers not solid at room temperature; other viscosity modifiers not solid at room temperature and chemically formed by esters, like phthalates, benzoates, sebacates, citrates, tartrates; vegetable oils; synthetic and natural fats; and their blends.

In a preferred sub-embodiment, the above mentioned oligomers and polymers, not solid at room temperature, of polyolefins from C2 to C20, are synthesised with metallocenic catalysts; or anyhow have a Polydispersity Index lower than 3.5 and preferably lower than 2.5. Viscosity modifiers of this type are manufactured and sold e.g. by ExxonMobil with the trade marks SpectraSyn and Elevast; by Ineos with the trade mark Durasyn; by Chevron Phillips with the trade mark Synfluid; by Clariant with marks like Licocene PPA 330.

Waxes

In a third embodiment of the present invention, the hot-melt adhesives disclosed herein comprise at least one wax or a blend of waxes at a level between zero and 10% by weight, and preferably between zero and 5% by weight.

In a further preferred sub-embodiment, said wax or blend of waxes is a polyolefinic wax or a blend of polyolefinic waxes, said polyolefinic wax/waxes moreover containing more than 50% by mole of ethene or propene and having a viscosity at 190° C. that is not higher than 2,000 mPa·s.

In an additional embodiment, said polyolefinic wax or blend of polyolefinc waxes, based on ethene or propene, is/are modified with maleic anhydride.

Other Optional Ingredients

The hot-melt adhesives according to the present invention can moreover comprise from 0.01% by weight and 10% by weight of at least one stabiliser, like anti-oxidants, photo-stabilizers, UV stabilizers, and their blends.

They can also further comprise up to 15% by weight of other optional additional ingredients, like mineral fillers, pigments, dyes, perfumes, surfactants, anti-static agents.

EXAMPLES

The present invention is better illustrated by the following examples, which are given merely for the purpose of illustration and are not to be regarded as limiting the scope of the invention or the manner in which it can be practiced. Unless specifically indicated otherwise, parts and percentages are given by weight.

EXAMPLES ACCORDING TO THE INVENTION

Example 1

The following hot-melt adhesive formulation, according to the present invention, was prepared by mixing its constituents in the molten state at 170° C.:

| Ingredient | % by weight on the total weight of the adhesive formulation | Nature and Supplier |
|---|---|---|
| Rextac RT 2830 | 53.0 | Monomodal non-isotactic butene-1 copolymer available from Rextac |
| Koattro PB M 1500M | 21.3 | Bimodal isotactic metallocene butene-1 polymer composition available from LyondellBasell |
| Eastotac H-100L | 23.7 | Hydrogenated aliphatic hydrocarbon tackifier available from Synthomer. |
| Irganox 1010 | 2.0 | Antioxidant available from BASF |

The hot-melt adhesive formulation of Example 1) comprises, as its polymeric base, a blend between two butene-1 polymers, Rextac RT 2830 and Koattro PB M 1500M.

Rextac 2830, available from Rextac (USA), is a non-isotactic butene-1 copolymer, synthesised with Ziegler-Natta catalysts, and it is believed to be composed by about 55% by mole butene-1 and 45% by mole propene. It has an amorphous character, an average Number Molecular Weight, Mn, equal to about 9,300 g/mole, and a Polydispersity Index, Mw/Mn, as great as 7.1. Moreover, Rextac 2830 shows a melt viscosity at 190° C. of 3,000 mPa·s and the following thermal properties, measured by DSC, after five days of aging under room conditions: an enthalpy of fusion of 22.1 J/g; a peak melting temperature of 40° C. and a glass transition temperature of −24.1° C.

Koattro PB M 1500M, available from LyondellBasell (The Netherlands) is believed to be a bimodal polymeric composition of isotactic butene-1, synthesised on metallocene catalysts, and having an average global Number Molecular Weight, Mn, equal to about 22,800 g/mole, and a global Polydispersity Index, Mw/Mn, equal to 2.3. Such bimodal polymeric composition is also believed to be constituted by a copolymer between butene-1 and ethene, at a level of ethene of about 13% by mole, and by a butene-1 homopolymer. During the polymerisation step, once synthesised said butene-1/ethene copolymer, it is then intimately blended, at an intermolecular level, with a butene-1 homopolymer, also synthesised in the same reactor, in a ratio such that the global content of ethene in the final polymeric composition, is about 10% by mole (or also about 5.3% by weight). Koattro PB M 1500M has a melt viscosity at 190° C. equal to 5,630 mPa·s, and the following thermal properties, measured by DSC, after five days of aging at room conditions: an enthalpy of fusion of 34.3 J/g; a peak melting temperature of 110° C. and a glass transition temperature of −41.4° C.

The hot-melt formulation of Example 1) further comprises 23.7% by weight of Eastotac H-100L, a hydrogenated aliphatic hydrocarbon tackifying resin available from Synthomer (USA). This tackifier has a Ring & Ball softening point of 100° C. and an average Number Molecular Weight, Mn, equal to 410 g/mole.

Finally, the above disclosed adhesive also comprises 2% by weight of the antioxidant Irganox 1010, available from BASF (Germany).

The adhesive formulation of Example 1) exhibits both excellent adhesive properties and excellent processability. In fact it can be processed, without any problem, on a pilot line, running at the very high speed of 250 m/minute and that reproduces the structure and the working conditions of a real industrial line for the manufacturing of absorbent hygienic articles like baby-diapers. When tested, under such processing conditions, for its Peel Strength, according to the method for the measurement of Peel Strength described above, the adhesive formulation of Example 1) exhibits an optimal Peel Strength equal to as much as 1.32 N/50 mm, a result that clearly shows the superior adhesive properties of this hot-melt (Table 1).

Such hot-melt adhesive has also very good cohesive and mechanical properties, measured at 23° C. after five days of aging at room conditions, as shown by a Toughness of 0.54 MJ/$m^3$, by a maximum stress (peak) of the stress-vs-elongation-at-break curve of 0.7 MPa and by an elongation at break of 157%. Furthermore, the hot-melt adhesive formulation of Example 1), has also the following properties: a melt viscosity at 170° C. equal to 3,880 mPa·s; a Ring & Ball Softening Point of 103.8° C.; a rheological setting temperature, measured at time zero and in decreasing temperature at the cooling speed of 2° C./minute and at the frequency of 1 Hz, equal to 48° C.; an elastic Modulus G', after five days of aging, measured at 23° C. and 1 Hz in increasing temperature at the heating speed of 2° C./minute, equal to 8.3 MPa.

Example 2

The following hot-melt adhesive formulation, according to the present invention, was prepared by mixing its constituents in the molten state at 170° C.:

| Ingredient | % by weight on the total weight of the adhesive formulation | Nature and Supplier |
|---|---|---|
| Rextac RT 2830 | 76.7 | Monomodal non-isotactic butene-1 copolymer available from Rextac |
| Koattro PB M 1500M | 21.3 | Bimodal isotactic metallocene butene-1 polymer composition available from LyondellBasell |
| Irganox 1010 | 2.0 | Antioxidant available from BASF |

The hot-melt adhesive formulation of Example 2 is based on a blend of the same butene-1-polymers already used in Example 1), blend that is obtained by just slightly varying the ratio between the two polymeric constituents. However Example 2), differently from Example 1), does not contain at all any tackifier; and in general, it does not contain at all any non-polymeric component at low molecular weight (as tackifiers, viscosity modifiers, waxes and the like, with an average Number Molecular Weight that typically is not greater than 2,500 g/mole), apart of course from a very small percent of the antioxidant Irganox 1010.

This absence of all low molecular weight constituents that are usually contained even in high quantities in hot-melt adhesives, gives this formulation, as it has been thoroughly explained above, additional and very peculiar and beneficial characteristics. In particular, as explained in the text of the previous paragraphs, this peculiar formulation of the adhesive of Example 2) gives it an optimum stability of its properties in time. In fact, the absence of all the low molecular weight ingredients, that tend with time to demix from the formulation and to migrate and bleed on its surface, assures an unusual constancy over time of all its main adhesive properties. Moreover, the absence of this bleeding out from the formulation of low molecular weight ingredients also prevents the generation of malodours and prevents possible effects of skin irritation, sensitisation, and also allergic and even toxic effects that can be easily generated when these bled substances contact the skin of a user.

In spite of the absence of any tackifier or of any viscosity modifier and plasticiser at low molecular weight, the formulation of Example 2) continues to have a relatively low melt viscosity, equal to 5,750 mPa·s at 170° C., and it can be easily processed, without problems, even on industrial lines operating at very high speeds, like 250 m/minute. Furthermore, even without tackifiers, this hot-melt exhibits also good adhesive properties, because, when tested for its Peel Strength, under the condition previously described, it provides an excellent Peel Strength equal to 1.19 N/50 mm (Table 1).

The absence of all low molecular weight components also further improves in Example 2) the already good cohesive and mechanical properties seen in the previous Example 1). In fact, the adhesive formulation of Example 2) shows a Toughness, still measured at 23° C. after five days of aging under room conditions, of 1.34 MJ/$m^3$; a maximum stress (peak) of the stress-vs-elongation-at-break curve equal to 1.4 MPa; and an elongation at break equal to 165%.

The hot-melt adhesive formulation of Example 2), shows also the following additional properties: a Ring & Ball Softening Point of 111.4° C.; a rheological setting temperature, measured at time zero and in decreasing temperature at the cooling speed of 2° C./minute and at the frequency of 1 Hz, equal to 73° C.; an elastic Modulus G', after five days of aging, measured at 23° C. and 1 Hz in increasing temperature at the heating speed of 2° C./minute, equal to 18.8 MPa.

Example 3

The following hot-melt adhesive formulation, according to the present invention, has been prepared by mixing its constituents in the molten state at 170° C.:

| Ingredient | % by weight on the total weight of the adhesive formulation | Nature and Supplier |
|---|---|---|
| Rextac RT 2830 | 53.0 | Monomodal non-isotactic butene-1 copolymer available from Rextac |
| Koattro PB M 8510M | 10.0 | Bimodal isotactic metallocene butene-1 polymer composition available from LyondellBasell |
| Eastotac H-100L | 35.0 | Hydrogenated aliphatic hydrocarbon tackifier available from Synthomer. |
| Irganox 1010 | 2.0 | Antioxidant available from BASF |

The hot-melt adhesive formulation of Example 3 is based on a blend of two butene-1 polymers equal or similar to the two polymers used in the two previous Examples.

The main difference of Example 3) is the fact that it substitutes the bimodal isotactic metallocene butene-1 polymer composition Koattro PB M 1500M, with an analogous bimodal isotactic metallocene butene-1 polymer composition Koattro PB M 8510M, of similar chemical composition. Koattro PB M 8510M substantially differs from Koattro PB M 1500M in its higher average Number Molecular Weight Mn that is believed to be equal to 66,700 g/mole. Other differences of Koattro PB M 8510M versus the previous Koattro at lower molecular weight, is a Polydispersity Index, Mw/Mn, equal to 2.1 and a much higher melt viscosity at 190° C. equal to 230,000 mPa·s. Its thermal properties, measured by DSC, after five days of aging at room conditions, are as follows: an enthalpy of fusion of 38.2 J/g; a peak melting temperature of 98.2° C. and a glass transition temperature of −36.4° C.

The use of Koattro PB M 8510M, with a significantly higher molecular weight Mn, compared to Koattro PB M 1500M, further improves the cohesive and mechanical properties of the hot-melt formulation, without affecting its very good processability even at the high speed of 250 m/minute as well as without impairing its excellent adhesive characteristics. It fact the molten viscosity of the formulation of Example 3) is 5,650 mPa·s and, when tested for its Peel Strength according to the previously described method, it provides a very good Peel Strength equal to 0.98 N/50 mm (Table 1).

The Toughness of the hot-melt in Example 3), measured as usual at 23° C. after five days of aging under room conditions, is of 5.84 MJ/m$^3$; its maximum stress (peak) of the stress-vs-elongation-at-break curve is equal to 0.9 MPa; and its elongation at break is very high and equal to 582%.

The hot-melt adhesive formulation of Example 3), shows also the following additional properties: a Ring & Ball Softening Point of 105.7° C.; a rheological setting temperature, measured at time zero and in decreasing temperature at the cooling speed of 2° C./minute and at the frequency of 1 Hz, equal to 42° C.; an elastic Modulus G', after five days of aging, measured at 23° C. and 1 Hz in increasing temperature at the heating speed of 2° C./minute, equal to 15.0 MPa.

COMPARATIVE EXAMPLES

Comparative Example 1

The following comparative hot-melt adhesive formulation has been prepared by mixing its constituents in the molten state at 170° C.:

| Ingredient | % by weight on the total weight of the adhesive formulation | Nature and Supplier |
|---|---|---|
| Rextac RT 2830 | 53.0 | Monomodal non-isotactic butene-1 copolymer available from Rextac |
| Koattro PB M 0801M | 21.3 | Monomodal isotactic, non-metallocene butene-1 homopolymer available from LyondellBasell |
| Eastotac H-100L | 23.7 | Hydrogenated aliphatic hydrocarbon tackifier available from Synthomer. |
| Irganox 1010 | 2.0 | Antioxidant available from BASF |

The hot-melt adhesive formulation of Comparative Example 1) reproduces the same formulation of the previous Example 1), according to the invention, with the only difference that the previous bimodal polymeric composition of isotactic butene-1, Koattro PB M 1500M, synthesised on metallocene catalysts and with a polydispersity index Mw/Mn of 2.3, has been replaced with Koattro PB M 0801M, which is monomodal isotactic, non-metallocenic, butene-1 homopolymer. Koattro PB M 0801M is believed to have an average Number Molecular Weight, Mn, of about 20,500 g/mole and a polydispersity index of 4.9. It shows also a melt viscosity at 190° C. equal to 47,000 mPa·s, an enthalpy of Fusion, at five days of aging, of 78.3 J/g, a DSC peak melting temperature of 120.9° C. and a glass transition temperature of −24.0° C.

The hot-melt adhesive formulation of Comparative Example 1), that has a melt viscosity at 170° C. equal to 7,500 mPa·s, when tested for Peel Strength according to the disclosed herein method, exhibits an exceedingly low adhesive strength, equal just to 0.15 N/50 mm (Table 1). Moreover it exhibits a toughness of 8.15 MJ/m$^3$, a maximum stress (peak) of the stress-vs-elongation-at-break curve of 1.9 MPa and an elongation at break that is 131%; a Ring & Ball Softening Point of 118.3° C.; a rheological setting temperature, measured at time zero and in decreasing temperature at the cooling speed of 2° C./minute and at the frequency of 1 Hz, equal to 55° C.; an elastic Modulus G', after five days of aging, measured at 23° C. and 1 Hz in increasing temperature at the heating speed of 2° C./minute, equal to 19.3 MPa.

Comparative Example 2

The following comparative hot-melt adhesive formulation has been prepared by mixing its constituents in the molten state at 170° C.:

| Ingredient | % by weight on the total weight of the adhesive formulation | Nature and Supplier |
|---|---|---|
| Koattro PB M 2500M | 53.0 | Bimodal isotactic metallocene butene-1 polymer composition available from LyondellBasell |
| Koattro PB M 1500M | 21.3 | Bimodal isotactic metallocene butene-1 polymer composition available from LyondellBasell |
| Eastotac H-100L | 23.7 | Hydrogenated aliphatic hydrocarbon tackifier available from Synthomer. |
| Irganox 1010 | 2.0 | Antioxidant available from BASF |

Also the hot-melt adhesive formulation of Comparative Example 2) reproduces the same formulation of the previous Example 1), according to the invention, with the only difference that the previous monomodal non-isotactic butene-1 copolymer Rextac RT 2830, with a polydispersity index Mw/Mn as high as 7.1, an enthalpy of Fusion, at five days of aging, of just 22.1 J/g and a DSC peak melting temperature not higher than 80° C. and more precisely equal to 40° C., etc., has been substituted with a bimodal isotactic metallocene butene-1 polymer composition, Koattro PB M 2500M, that is fully similar to the other main polymeric component present in the formulation, i.e. similar to Koattro PB M 1500M, from which it differs just in its average Number Molecular Weight, equal to about 19,600 g/mole, and for its melt viscosity at 190° C., that is 3,250 mPa·s, almost equal to the one of Rextac RT 2830.

The bimodal polymeric composition of isotactic butene-1, synthesised on metallocene catalysts, Koattro PB M 2500M, has moreover a polydispersity index Mw/Mn as low as 2.0, an enthalpy of Fusion, at five days of aging, of 69.4 J/g, a DSC peak melting temperature well above 80° C. and more precisely equal to 102.7° C. and a glass transition temperature of −26.7° C. It is also believed to have a global content of ethene comonomer of about 7% by mole (i.e. about 3.6% by weight).

The formulation of Comparative Example 2) shows a Peel Strength of 0.66 N/50 mm (Table 1), a value that is still significantly lower than the Peel Strengths shown by the three previous Examples according to the invention, but that is also considerably higher than the fully inadequate Peel shown by the previous Comparative Example 1).

However, the greatest problem of the Comparative Example 2) is the fact that, during its application by slot-die coating, in the molten state at 165° C., on a pilot line running at the industrial speed of 250 m/minute, this formulation showed an unacceptably massive phenomenon of "build-up" (known also as "die-drool"). I.e., as well known by all persons with an average expertise in the extrusion of polymers and of polymeric formulations, this very negative phenomenon consists in the fact that a part of the extruded polymeric formulation remains adhered on the metal of the extrusion-head itself, and it builds up in masses of increasing weight and volume, on the metallic surface just outside and around the extrusion holes. Said masses of built-up material, that in the meanwhile also start to degrade owing to the high temperature on long times, occasionally and irregularly come off from the extrusion-head, stick on the underlying running substrate, that takes these lumps of material away, while the build-up process restarts. In this way, the quality of the finished product is irretrievably spoiled, often at unacceptable levels, by this substantially chaotic and uncontrollable phenomenon, both because the coating is a grossly irregular film with uneven thickness, and because of the presence at random gaps of big lumps of adhesive, that moreover are also strongly degraded.

Therefore most likely the apparently relatively high average Peel Strength of 0.66 N/50 mm recorded for Comparative Example 2) is actually "a falsely positive result" due to the fact that the very irregular coating of the extruded adhesive, with the presence of big lumps, scattered here and there, slants and falsifies the average read value of the overall average Peel Strength with local high peaks of strength, due to the lumps.

Moreover, also several of the mechanical and thermal properties of Comparative Example 2) are worse than the ones of the corresponding Example 1), according to the invention, especially its elongation at break that is just 85% and its rheological setting temperature, measured at time zero and in decreasing temperature at the cooling speed of 2° C./minute and at the frequency of 1 Hz, that is unacceptably low and equal to only 26° C.

The hot-melt adhesive formulation of Comparative Example 2) shows also the following additional properties: a toughness of 4.5 $MJ/m^3$; a maximum stress (peak) of the stress-vs-elongation-at-break curve equal to 3.3 MPa; a melt viscosity at 170° C. equal to 3,500 mPa·s; a Ring & Ball Softening Point of 104.0° C.; an elastic Modulus G', after five days of aging, measured at 23° C. and 1 Hz in increasing temperature at the heating speed of 2° C./minute, equal to 48.3 MPa.

Comparative Example 3

The following comparative hot-melt adhesive formulation was prepared by mixing its constituents in the molten state at 170° C.:

| Ingredient | % by weight on the total weight of the adhesive formulation | Nature and Supplier |
|---|---|---|
| Rextac RT 2830 | 66.3 | Monomodal non-isotactic butene-1 copolymer available from Rextac |
| Tafmer PN-20300 | 8.0 | Monomodal metallocene butene-1 copolymer available from Mitsui Chemicals |
| Eastotac H-100L | 23.7 | Hydrogenated aliphatic hydrocarbon tackifier available from Synthomer. |
| Irganox 1010 | 2.0 | Antioxidant available from BASF |

Also, the hot-melt adhesive formulation of Comparative Example 3) is conceptually reproducing the formulations of the previous Examples according to the invention. However, in it the bimodal isotactic metallocene butene-1 polymer compositions Koattro PB M 1500M or Koattro PB M 8510M, have been replaced by Tafmer PN-20300, a monomodal metallocene butene-1 polymer which is believed to be a copolymer between butene-1, propene and ethene, containing about 30% by mole of butene-1, about 49% by mole of propene and about 21% by mole of ethene. Tafmer PN-20300 is also believed to have an average Number Molecular Weight Mn equal to 72,000 g/mole and a polydispersity index equal to 2.5. It has moreover an unacceptably high melt viscosity at 190° C. of 810,000 mPa·s, a DSC enthalpy of Fusion, at five days of aging, of 33.1 J/g, a very high peak melting temperature equal to 160.6° C. and a glass transition temperature of −28° C.

The hot-melt of Comparative Example 3) proved to be completely non processable at all the typical processing temperatures used for processing hot-melt adhesives and generally comprised between 130° C. and 180° C. This is essentially due to its unacceptably high melt viscosity that e.g. at 170° C. is as much as 28,800 mPa·s. Therefore, it was impossible to obtain any Peel Strength according to the method for Peel Strength used herein.

Moreover, the adhesive formulation of Comparative Example 3) exhibits also an unacceptably high Ring & Ball Softening Point, equal to as much as 149.4° C. It has a toughness, after five days of aging, equal to 6.05 $MJ/m^3$, a maximum stress (peak) of the stress-vs-elongation-at-break curve of 0.9 MPa and an elongation at break that is 596%; a rheological setting temperature, measured at time zero and in decreasing temperature at the cooling speed of 2° C./minute and at the frequency of 1 Hz, equal to 88° C.; an elastic Modulus G', after five days of aging, measured at 23° C. and 1 Hz in increasing temperature at the heating speed of 2° C./minute, equal to 8.5 MPa.

TABLE 1

Peel Strength (measured according to the method described above)

| Sample | Peel Strength (N/50 mm) |
|---|---|
| Example 1 (invention) | 1.32 |
| Example 2 (invention) | 1.19 |
| Example 3 (invention) | 0.98 |
| C. Example 1 (comparative) | 0.15 |
| C. Example 2 (comparative) | 0.66 (Irregular extrusion and coating) |
| C. Example 3 (comparative) | Non processable |

The invention claimed is:

1. Hot melt adhesive, characterised in that it comprises a polymer blend consisting of at least two butene-1 polymers, A) and B), such blend comprising:

A) from 5% to 95% by weight, referred to the overall weight of the blend, of at least one non-isotactic butene-1 copolymer, having a polydispersity index Mw/Mn not lower than 3.5 and a monomodal composition, such copolymer consisting of butene-1 with one or more alpha-olefins selected from ethene, propene and alpha-olefins from C5 to C12, said copolymer furthermore having a content of copolymerised comonomer(s) not lower than 20% by mole, a viscosity at 190° C. comprised between 1,000 mPa·s and 200,000 mPa·s and being further characterised by the following thermal properties, measured by DSC after five days of aging at 23° C. and 50% relative humidity:
an enthalpy of Fusion not greater than 40 J/g,
a peak melting temperature not higher than 80° C.;
a glass transition temperature Tg not higher than −10° C.;

B) between 95% and 5% by weight, referred to the overall weight of the blend, of at least one polymeric composition of isotactic butene-1, having a global polydispersity index Mw/Mn lower than 3.5 and a bimodal composition, such bimodal polymer composition comprising:

B1) between 10% and 90% by weight of a butene-1 copolymer with one or more comonomers selected from ethene, propene and alpha-olefins with a number of Carbon atoms equal to or greater than five, said copolymer B1) having a content of copolymerised comonomer(s) lower than 20% by mole and a polydispersity index Mw/Mn lower than 3.5;

B2) between 90% and 10% by weight of a butene-1 homopolymer or a butene-1 copolymer with one or more comonomers selected from ethene, propene and alpha-olefins having a number of Carbon atoms equal to or greater than five, said homopolymer or copolymer B2) having a content of copolymerised comonomer(s) not greater than 5% by mole and a polydispersity index Mw/Mn lower than 3.5;

such polymeric composition of isotactic butene-1, having a bimodal composition, a viscosity at 190° C. ranging comprised between 1,000 mPa·s and 300,000 mPa·s and being further characterised by the following thermal properties, measured by DSC after five days of aging at 23° C. and 50% relative humidity:
an Enthalpy of Fusion greater than 20 J/g,
a melting peak temperature higher than 90° C.,
a glass transition temperature Tg not higher than −20° C.

2. The hot melt adhesive as in claim 1), characterised in that the isotactic polymeric composition of butene-1, B), having a global polydispersity index Mw/Mn lower than 3.5 and a bimodal composition and which comprises the two polymers B1) and B2), has a ponderal ratio between its components B1) and B2), such that the global content of copolymerised comonomer(s) different from butene-1, and referred to the sum of B1) plus B2), is lower than 20% by mole.

3. The hot melt adhesive as in claim 1), characterised in that the copolymer of non-isotactic butene-1, A), having a polydispersity index Mw/Mn not lower than 3.5 and a monomodal composition, has a numeral average molecular weight Mn not greater than 30,000 g/mole.

4. The hot melt adhesive as in claim 1) characterised in that the isotactic composition of butene-1, B), having a Polydispersity Index lower than 3.5 and a bimodal composition, and that comprises the two polymers B1) and B2), has an average Number Molecular Weight Mn not greater than 150,000 g/mole.

5. The hot melt adhesive as in claim 1, characterised in that the polymer blend of at least two butene-1 polymers, A) and B), contains from 10% to 95% by weight of the non-isotactic butene-1 copolymer A), and from 5% to 60% by weight of the bimodal isotactic polymeric composition of butene-1, B).

6. The hot melt adhesive as in claim 1, characterised in that the polymer blend of at least two butene-1 polymers, A) e B), has a ponderal ratio between A) and B) greater than 1.

7. The hot melt adhesive as in claim 1, characterised in that the polymer blend of at least two butene-1 polymers, A) and B), comprises also from zero to 30% by weight of at least one butene-1 homopolymer or copolymer, with one or more alpha-olefins selected among ethene, propene and the olefins from C5 to C12, said homopolymer or copolymer C1) having a content of copolymerised comonomer(s) lower than 20% by mole and having a polydispersity index greater than 3.5, an enthalpy of fusion after five days greater than 30 J/g, a melting peak temperature higher than 80° C. and a glass transition temperature Tg not higher than −10° C., said thermal properties being measured by DSC.

8. The hot melt adhesive as in claim 7), characterised in that said butene-1 homopolymers or copolymers C1) or C2) have a monomodal composition.

9. The hot melt adhesive as in claim 1, characterised in that the polymer blend of at least two butene-1 polymers, A) and B), comprises also from zero to 30% by weight of at least one butene-1 homopolymer or copolymer, with one or more alpha olefins selected among ethene, propene and the olefins from C5 to C12, said homopolymer or copolymer C2) having a content of copolymerised comonomer(s) not lower than 20% by mole and having a polydispersity index lower than 3.5, an enthalpy of fusion after five days not greater than 30 J/g, a melting peak temperature not higher than 90° C. and a glass transition temperature Tg not higher than −20° C., said thermal properties being measured by DSC.

10. The hot melt adhesive as claim 1, characterised in that it further comprises from zero to 30% by weight of one or more polymers (homopolymers, copolymers and their blends) that do not contain butene-1.

11. The hot melt adhesive as in claim 10), characterised in that such polymer(s) containing no butene-1 is/are polyolefin(s).

12. The hot melt adhesive as in claim 10), characterised in that such polyolefin(s) containing no butene-1 is/are a propene homopolymer, an ethene and propene copolymer or a copolymer between propene and an alpha-olefin from C5 to C12 or between propene and ethene and an alpha-olefin from C5 to C12.

13. The hot melt adhesive as in claim 10, characterised in that such polyolefin(s) contain(s) hexene.

14. The hot melt adhesive as in claim 10, characterised in that such polyolefin(s) is/are a propene and ethene copolymer(s) having a heterophasic structure.

15. The hot melt adhesive as in claim 1, characterised in that the sum of all the polymers listed in said claims makes up between 5% and 99.5% by weight of the overall hot melt adhesive.

16. The hot melt adhesive as in claim 1, characterised in that it also comprises from zero to 70% by weight of at least one tackifying resin.

17. The hot melt adhesive as in claim 16), characterised in that the tackifying resin is selected from non-hydrogenated, partially hydrogenated or fully hydrogenated aliphatic hydrocarbon resins; non-hydrogenated, partially hydrogenated or fully hydrogenated aromatic hydrocarbon resins; non-hydrogenated, partially hydrogenated or fully hydrogenated aliphatic-aromatic hydrocarbon resins; non-hydrogenated, partially hydrogenated or fully hydrogenated polyterpene resins and modified polyterpene resins; non-hydrogenated, partially hydrogenated or fully hydrogenated rosins and esters thereof; and blends thereof.

18. The hot melt adhesive, as in claim 16), characterised in that the tackifying resin or the blend of tackifying resins has a Ring & Ball softening temperature ranging between 5° C. and 160° C.

19. The hot melt adhesive as in claim 1, characterised in that it also comprises from zero to 40% by weight of at least one viscosity modifier or a blend of viscosity modifiers that is/are not solid at room temperature (23° C.).

20. The hot melt adhesive as in claim 19), characterised in that the viscosity modifier, which is not solid at room temperature (23° C.), or the blend of said modifiers, is/are selected from: paraffinic mineral oils; naphthenic mineral oils; paraffinic and naphthenic hydrocarbons not solid at room temperature (23° C.), and blends thereof; oligomers and polymers not solid at room temperature (23° C.) of polyolefins from C2 to C20 and their co-oligomers and copolymers not solid at room temperature (23° C.); viscosity modifiers not solid at room temperature (23° C.) consisting of esters; vegetable oils; natural and synthetic fats; and blends thereof.

21. The hot melt adhesive as in claim 20), characterised in that the oligomers and polymers not solid at room temperature (23° C.) of polyolefins from C2 to C20 and their co-oligomers and copolymers not solid at room temperature (23° C.) have a polydispersity index not greater than 3.5.

22. The hot melt adhesive as in claim 1, characterised in that it comprises from zero to 10% by weight, of a wax or of a blend of waxes.

23. The hot melt adhesive as in claim 22), characterised in that the wax contains more than 50% by mole of ethene or of propene and it has a viscosity at 190° C. not greater than 2,000 mPa·s.

24. The hot melt adhesive as in claim 23), characterised in that the wax, which contains more than 50% by mole of ethene or of propene, is modified with maleic anhydride.

25. The hot melt adhesive as in claim 1, characterised in that it comprises up to 10% by weight of at least a stabiliser.

26. The hot melt adhesive as in claim 1, characterised in that it contains from 60% to 99.5% by weight of polymers.

27. The hot melt adhesive as in claim 1, characterised in that it contains from zero to 35% by weight, of the sum between tackifying resins plus viscosity modifiers plus waxes.

28. The hot melt adhesive as in claim 1, characterised in that it comprises between zero and 10% by weight of at least one additional component, selected among mineral fillers, pigments, dyes, perfumes, surfactants, antistatic agents and blends thereof.

29. The hot melt adhesive, as in claim 1, characterised in that it has a Brookfield viscosity at 170° C. not greater than 20,000 mPa·s.

30. The hot melt adhesive as in claim 1, characterised in that it has a Ring & Ball softening temperature not greater than 135° C.

31. The hot melt adhesive as in claim 1, characterised in that, after aging for five days at 23° C. and 50% relative humidity, it has a stress-vs-elongation-at-break curve, measured at 23° C. and at the frequency of 0.1 Hz, that has a toughness not lower than 0.1 $MJ/m^3$.

32. The hot melt adhesive as in claim 31), characterised in that it has a maximum stress (peak) of the stress-vs-elongation-at-break curve at 23° C. and 0.1 Hz, not lower than 0.15 Mpa.

33. The hot melt adhesive as in claim 31), characterised in that it has an elongation at break at 23° C. and 0.1 Hz, not below 50%.

34. The hot melt adhesive as in claim 1, characterised in that it has a rheological setting temperature Tx, measured at time zero and in decreasing temperature at the cooling speed of 2° C./minute and at the frequency of 1 Hz, not lower than 30° C.

35. The hot melt adhesive as in claim 1, characterised in that, after aging for five days at 23° C. and 50% relative humidity, it has an elastic modulus G' not lower than 0.2 MPa, when said elastic modulus is measured at 23° C. and 1 Hz in increasing temperature at the heating speed of 2° C./minute.

36. Glued structure, comprising:

a first substrate;

a second substrate;

the hot melt adhesive as in claim 1, that glues the first substrate to the second substrate, and that, if applied at a basis weight ranging from 0.5 $g/m^2$ to 50 $g/m^2$, gives to the glued structure a Peel Strength, measured after five days of aging at 23° C. and 50% relative humidity, greater than 0.25 N per 50 mm width.

37. The glued structure as in claim 36), characterised in that at least one of the two substrates is a porous or a fibrous substrate or a nonwoven or a perforated film that has a bi-dimensional or a tridimensional structure.

38. Absorbent hygienic article characterised in that it comprises a glued structure as in claim 36.

39. Absorbent hygienic article characterised in that it comprises the hot melt adhesive as in claim 1.

40. The article as in claim 39), characterised in that said article is an absorbent diaper for babies or children, training pants for toddlers, an absorbent diaper for incontinent adults, an absorbent article for feminine hygiene.

41. The absorbent hygienic articles as in claim 39, characterised in that the hot melt adhesive is used at least for one of the following uses: i) general construction adhesive for the whole article; ii) for the gluing of elastic components (threads, ribbons, films or elastic panels, etc.); iii) for consolidating/immobilising and secure also during use the integrity of the absorbent layers of the absorbent hygienic articles; iv) for the gluing of perforated films having a bi-dimensional or a tridimensional structure; v) for the mutual gluing of two nonwoven fabrics or of two plastic films or for the gluing of nonwoven fabrics to plastic films.

42. Article comprising the hot melt adhesive as in claim 1, characterised in that said article is an absorbent mat or sheet or surgical laminate for medical use or a product for covering and protecting wounds.

43. Article comprising the hot melt adhesive as in claim 1, characterised in that said article is a mattress or a component thereof.

44. Article comprising the hot melt adhesive as in claim 1, characterised in that said article is a packaging.

* * * * *